United States Patent [19]

Lein, Jr.

[11] Patent Number: 4,994,574
[45] Date of Patent: Feb. 19, 1991

[54] PREPARATION OF ISOTHIAZOLONES

[76] Inventor: George M. Lein, Jr., 80 Oxbow Cir., Chalfont, Pa. 18914

[21] Appl. No.: 126,051

[22] Filed: Nov. 27, 1987

[51] Int. Cl.<sup>5</sup> .......................................... C07D 275/02
[52] U.S. Cl. ................................... 548/213; 562/840
[58] Field of Search ........................................ 548/213

[56] References Cited

U.S. PATENT DOCUMENTS 3,761,488 9/1973 Lewis et al. .......................... 548/213
3,849,430 11/1974 Lewis et al. .......................... 548/213

FOREIGN PATENT DOCUMENTS 95907 12/1983 European Pat. Off. .
121524 3/1966 Fed. Rep. of Germany ...... 548/213

OTHER PUBLICATIONS

Luttringhaus et al., Agnew. Chem. Int. E. I. Eng. 3, 67 (1964).
Luttringhaus et al., Ann. Chem. 679, 123 (1964).
J. Organic Chem. 28, 1901 (1963).

*Primary Examiner*—Diana G. Rivers

[57] ABSTRACT

Preparation of 3-isothiazolones by a single-kettle synthesis from a 3,3'-dithiodipropionic acid, a 3-thiopropionic acid, or their related acid halide by reacting sequentially with a thionyl halide (if the (di)acid halide has not previously been formed), followed by reaction with a halogenating agent, then a primary amine and base, and then with a halogenating agent.

18 Claims, No Drawings

PREPARATION OF ISOTHIAZOLONES

This invention relates to a process for the preparation of 3-isothiazolones by a single-kettle synthesis from a 3,3'-dithiodipropionic acid, a 3-thiopropionic acid, or their related acid halide by reacting sequentially with thionyl halide (if the (di)acid halide has not previously been formed), followed by reaction with about one equivalent of a halogenating agent, then about two equivalents of primary amine and base, and then with a halogenating agent (about two equivalents) to achieve the unhalogenated isothiazolone. Preparation of a (di)-thiopropion-N,N'-diamide as a separate step is avoided.

If the (di)acid is used as the starting material, isolation and handling of the hydrolytically sensitive (di)acid chloride can be avoided. Further halogenation to the 5-halo- or 4,5-dihaloisothiazolone is also possible, either by addition of additional halogen or halogenating agent in the final stage, by further treatment of the isolated unhalogenated isothiazolone, or by co-feed of the intermediate after reaction with amine, along with additional halogen or halogenating agent, to a second reaction vessel.

2-Substituted isothiazolones, 4-halo-, 5-halo-, and 4,5-dihaloisothiazolones are well-known as efficacious chemicals for the control of living organisms, especially as biocidal chemicals. See for example U.S. Pat. Nos. 4,205,431; 4,265,899.

A conventional route to manufacture, as described inter alia in U.S. Pat. No. 3,761,488 and European Patent Application No. 95907, involves the preparation of a 3-mercapto-N-substituted propionamide (or 3,3'-dithio-N,N'-substituted propionamide), followed by halogenation to produce the desired non-halogenated isothiazolone product. Preparation of the halogenated or dihalogenated isothiazolone can be accomplished by use of higher ratios of halogen/amide. Preparation of the mercaptopropionamide may require several preparative steps, involving costly or difficultly obtainable intermediates, especially when the amine functionality needed to form the amide is less reactive, such as when it is cycloalkyl or aryl.

Halogen includes chlorine or bromine or both; chlorine is the preferred halogen. The same definition of halogen applies to halogenating agents.

Luttringhaus et al., [*Angew. Chem. Int. Ed. Eng.*, 3, 67 (1964); *Liebigs Ann. Chem.* 679, 123 (1964)] reported low yields of saturated isothiazolidines by sequential, separate kettle reaction of dithiodiacid with thionyl chloride, then chlorine, and then amine with pyridine base but did not carry the reaction through to the active isothiazolones.

In a similar manner, Kharasch et al. [*J. Org. Chem.*, 28, 1901 (1963)] produced a saturated six-membered ring from a 4-thiobutyric acid precursor.

This invention provides a new path to the known biocidally active isothiazolones which have a variety of uses including uses in cooling towers, paper mills, metal working, oil fields, latex, cosmetics, house cleaners, laundry, textile, plastic and resins, wood, leather and hides, photography, fuel, paints, swimming pools, medical devices, pharmaceuticals, food and feed preservations, disinfectants and sanitizers.

The process involved the following reaction sequence:

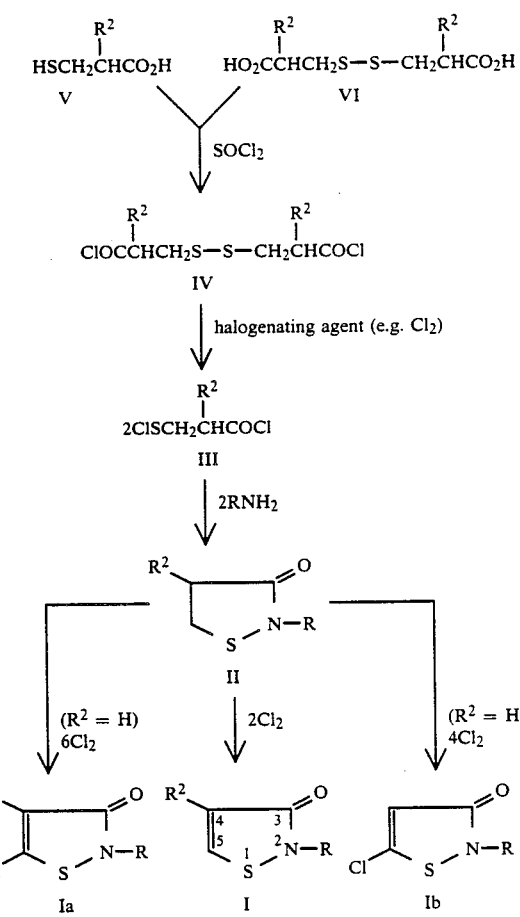

As starting primary amines in the present reaction, there may be used alkyl amines, preferably $C_1$ to $C_8$ alkylamines, cycloalkyl amines, preferably cyclohexyl amine, aryl amines, such as phenyl amine, 4-chlorophenyl amine, and the like, alkaryl amines, such as benzyl amine, and other moieties which will not interfere with the halogenation/cyclization reaction. Particularly preferred is n-octylamine. (The amine must be a primary amine for the desired product to be obtained.)

As suitable dithiodiacids (VI, supra), 3,3'-dithiodipropionic acid is most preferred, especially if it is desired to convert the resulting isothiazolone to chlorinated derivatives, such as 4,5-dichloroisothiazolone. Other starting acids may include 3,3'- dithio-2,2'-dialkyldipropionic acid, 3,3'-dithio-2,2'-dichlorodipropionic acid and the like. Other groups may be substituted in the 2 and/or 2' position if they do not interfere with the halogenation or ring closure reactions. Starting with dithiodimethylpropionic acid and extending the final halogenation reaction will result in the formation of the desirable 4-methyl-5-halo-2-substituted isothiazolone. Such dithiodiacids are commercially available or readily prepared from published procedures.

As suitable thioacids (V, supra), 3-thiopropionic acid is most preferred, especially if it is desired to convert the isothiazolone to chlorinated derivatives, such as the 4,5-dichloroisothiazolone. Other starting acids may include 3-thio-2-(lower alkyl)propionic acid and 3-thio-2-chloropropionic acid. Other groups may be substituted in the 2-position if they do not interfere with the halogenation/ring closure reactions. Starting with, 3-thio-2-methylpropionic acid and extending the final halogenation reaction will result in the formation of the desired 4-methyl-5-halo-2-substituted isothiazolone.

Thioacids are commercially available or readily prepared from published procedures. The corresponding acid halides are also suitable starting materials.

If thionyl halides are used either to prepare the (di)acid halide (IV, supra) in situ or separately, thionyl chloride and thionyl bromide are preferred with; thionyl chloride being most preferred. It is possible to prepare the (di)acid halide by other means, such as with phosphorus trichloride, phosphorus tribromide, or acetyl chloride, but the by-products of this conversion are less desirable when the one-kettle synthesis sequence is continued.

The diacid halide (IV) is then treated with a halogenating agent to afford the halothio propionyl halide (III, supra). The halogenating agent is preferably chlorine or bromine; with chlorine being most preferred. Other halogenating agents include sulfuryl chloride, sulfuryl bromide, N-chlorosuccinimide, N-bromosuccinimide, and the like.

It is necessary to use an acid scavenger to react with any excess acid. Any organic or inorganic base may be used as the scavenger; tertiary amines and nitrogenous cyclic compounds unaffected by the reaction conditions are preferred, with trialkyl amines being most preferred.

The halothiopropionyl halide (III, supra) is then treated with an amine of the formula; RNH$_2$, where R is as defined above, to afford the ring closed isothiazidine (II, supra) which is halogenated to afford the desired, active isothiazolone (I, supra).

The reaction sequence (halogenation;amidation-halogenation) is conducted at a temperature in the range of from about −20° C. to about 35° C. to minimize side reactions, although temperatures outside that range may be used. Inert or substantially inert solvents may be used, such as halobenzenes for example, chlorobenzene and the like or halo aliphatics. Reaction times for the sequence are of the order of from about one-half hour to about three hours per step, (the formation of the (di)acid halide in situ may be conducted over a longer time period, such as from about one to about ten hours).

The ratios of (di)acid or (di)acid halide to halogen are kept at about 1:1 during the initial addition of halogen. At least two moles of reactive amine and an equivalent amount of acid scavenger are then added. The final halogenation is best controlled by using about two moles of halogen when the desired product is the non-halogenated isothiazolone. The non-halogenated isothiazolone may be isolated, stabilized, and purified by known methods, or may be used directly for further halogenation.

If the 5-haloisothiazolone (Ib, supra) is desired, an additional four equivalents of halogenating agent may be added during the final reaction step. A preferred method would be to add the crude unhalogenated isothiazidine concurrently with about four equivalents of halogen to a second reaction vessel, in-line with the first, so that the overall reaction is conducted in one operation.

If it is desired to prepare the 4,5-dihaloisothiazolone (Ib, supra) without isolation of any intermediate, the unhalogenated aminated intermediate may be added together with the necessary additional halogen (about six equivalents) into a second reaction vessel, as described above for the 5-halo compound.

EXPERIMENTAL EXAMPLE 1

Preparation of 3-n-Octylisothiazolone from 3,3′-Dithiodipropionic acid

To a 500 ml flask fitted with a mechanical stirrer, nitrogen inlet, and an outlet to a 10% sodium hydroxide trap was charged 20g(0.095M) of 3,3′-dithiodipropionic acid, 200 ml of chlorobenzene and 0.25 ml of pyridine. An addition funnel containing 24.9 g (0.21 M) of thionyl chloride was added and the thionyl chloride was added dropwise. The mixture was warmed to 45° C. and stirred for 2.5 hours. The mixture was not homogeneous and was stirred overnight. (The reaction was still not quite homogeneous but was carried on at this point.) The mixture was reheated to 45° C. and sparged for 15 min with nitrogen. The remaining thionyl chloride was removed by stripping under house vaccuum for 1 hr and then 50 ml of chlorobenzene was charged. The mixture was cooled to −20° C. and 6.8 g (0.096 M) of chlorine was added over 16 min. After stirring 0.5hr the mixture was warmed to 0°–5° C. and a solution of 24.6 g (0.188 M) of n-octyl amine and 9.2 g (0.188 M) of triethyl amine in 100 ml of chlorobenzene was added dropwise such that the reaction temperature remained below 5° C. (addition time 1.75 hr). The solution was allowed to warm and then heated to 35° C. During this time the reaction thickened and then thinned out. Chlorine (13.5 g, 0.19 M) was then fed over 40 min at 35° C. and the mixture was stirred for an additional 1 hr. The reaction mixture was washed with 3×400 ml of water and then the solvent was removed under vaccuum to yield 36g of 3-n-octylisothiazolone as a dark oil. Analysis by capillary gas chromatography indicated a yield of 21.8 g (53.7%) of 3-n-octylisothiazolone.

EXAMPLE 2

Preparation of 3,3′-Dithiodipropionyl chloride

To a 300 ml round bottom flask fitted with a mechanical stirrer, nitrogen inlet and an outlet to a 10% sodium hydroxide trap was charged 169 g (1.42 M) of thionyl chloride and 100 g (0.48 M) of 3,3′-dithiodipropionic acid. The slurry was stirred and 0.5 ml of pyridine was charged. The mixture was stirred overnight. Excess thionyl chloride was then removed under house vacuum at room temperature until bubbling ceased and then for an additional 1.5 h at 40°–50° C. The resulting orange liquid of 3,3′-dithiodipropionyl chloride was used in Example 3 without further purification.

EXAMPLE 3

Preparation of 3-n-Octylisothiazolone

The process of Example 1 was repeated, except that the product of Example 2 was diluted with chlorobenzene, cooled to −20° C. and chlorinated. Analysis indicated a 59.6% yield of 3-n-octylisothiazolone.

In a similar manner, cyclohexylamine may be substituted for n-octylamine to afford 3-cyclohexylisothiazolone.

EXAMPLE 4

Preparation of 3-n-Octylisothiazolone from 3-thiopropionic acid

By following substantially the procedure of Example 1 and by substituting 3-thiopropionic acid for the dithiodiacid described therein a white solid of 3-n-octyliso-thiazolone precipitated during the exothermic portion of the reaction. Analysis of the final reaction mixture by high pressure liquid chromatography indicates a 45.9% yield of the 3-n-octylisothiazolone.

What is claimed is:

1. A process for preparing a compound of the formula:

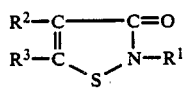

where $R^1$ is alkyl, substituted alkyl, aryl, substituted aryl, cycloalkyl, substituted cycloalkyl, or alkaryl and $R^2$ is H, halo or alkyl, $R^3$ is hydrogen or halo, which comprises treating a compound of the formula:

wherein $R^2$ is as defined above and X is halo, first with one equivalent of a halogenating agent, followed by the addition of a mixture of an acid scavenger and two equivalents of an amine of the formula: $R^1\text{-}NH_2$ wherein $R^1$ is as defined above and finally adding from two to six equivalents of halogenating agent.

2. The process of claim 1 where X is chloro.

3. The process of claim 1 wherein $R^2$ is H and X is chloro.

4. The process of claim 1 wherein $R^2$ is lower alkyl.

5. The process of claim 1 wherein the $R^1$ is alkyl or cycloalkyl.

6. The process of claim 5 wherein $R^1$ is n-octyl.

7. The process of claim 5 wherein $R^1$ is cyclohexyl.

8. The process of claim 1 where the dithiodiacid halide is formed in situ by reacting thionyl halide with $HSCH_2CHR_2COOH$.

9. A process for the preparation of 2-substituted-5-halo- isothiazolones of the formula

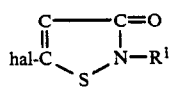

where $R^1$ is alkyl, substituted alkyl, aryl, substituted aryl, cycloalkyl, substituted cycloalkyl, or alkaryl which comprises treating a compound of the formula:

wherein X is halo, first with one equivalent of a halogenating agent, followed by the addition of about two equivalents of an amine of the formula $R^1\text{-}NH_2$ wherein $R^1$ is as defined above in combination with an acid scavenger and finally, adding four equivalents of a halogenating agent.

10. The process of claim 9 where halo is chloro and $R^1$ is $C_1\text{-}C_8$ alkyl or cyclohexyl.

11. A process for preparing a compound of the formula:

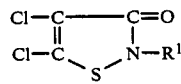

where $R^1$ is alkyl, substituted alkyl, aryl, substituted aryl, cycloalkyl, substituted cycloalkyl, or alkaryl, which comprises treating a compound of the formula:

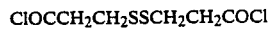

first with one equivalent of a halogenating agent, followed by the addition of about two equivalents of an amine of the formula $R^1\text{-}NH_2$ in combination with an acid scavenger, then treating the mixture with about six equivalents of a chlorinating agent.

12. The process of claim 11 wherein $R^1$ is $C_1\text{-}C_8$ alkyl or cyclohexyl.

13. A process for preparing a compound of the formula:

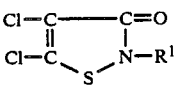

where $R^1$ is alkyl, substituted alkyl, aryl, substituted aryl, cycloalkyl, substituted cycloalkyl, or alkaryl, which comprises treating a compound of the formula:

first with one equivalent of a halogenating agent, followed by the addition of about two equivalents of an amine of the formula $R^1\text{-}NH_2$ in combination with an acid scavenger, then adding this reaction mixture, at about equal rates with about six equivalents of a chlorinating agent to a second vessel.

14. The process of claim 13 wherein R is $C_1\text{-}C_8$ alkyl or cycloalkyl.

15. A process for preparing a compound of the formula:

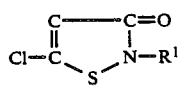

where $R^1$ is alkyl, substituted alkyl, aryl, substituted aryl, cycloalkyl, substituted cycloalkyl, or alkaryl which comprises treating a compound of the formula:

first with about one equivalent of chlorine, followed by the addition of two equivalents of an amine of the formula $R^1\text{-}NH_2$ in combination with an acid scavenger and finally treating the resulting mixture with about four equivalents of chlorine.

16. The process of claim 15 where $R^1$ is $C_1\text{-}C_8$ alkyl or cyclohexyl.

17. A process for preparing a compound of the formula:

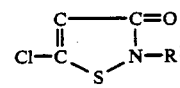

where $R^1$ is alkyl, substituted alkyl, aryl, substituted aryl, cycloalkyl, substituted cycloalkyl, or alkaryl which comprises treating a compound of the formula:

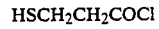

first with about one equivalent of chlorine, followed by the addition of two equivalents of an amine of the formula $R^1\text{-}NH_2$ in combination with an acid scavenger, then adding this reaction mixture at about equal rates with about 4 equivalents of a chlorinating agent to a second vessel.

18. The process of claim 17 wherein $R^1$ is $C_1\text{-}C_8$ alkyl or cyclohexyl.

* * * * *